US00PP22595P2

(12) United States Plant Patent
Tibbenham

(10) Patent No.: US PP22,595 P2
(45) Date of Patent: Mar. 20, 2012

(54) ***LEUCANTHEMUM* PLANT NAMED 'ENGELINA'**

(50) Latin Name: ***Leucanthemum* hybrid**
Varietal Denomination: Engelina

(76) Inventor: Irene Tibbenham, Eye (GB)

( * ) Notice: Subject to any disclaimer, the term of this patent is extended or adjusted under 35 U.S.C. 154(b) by 0 days.

(21) Appl. No.: 12/807,819

(22) Filed: Sep. 14, 2010

(51) Int. Cl.
*A01H 5/00* (2006.01)

(52) U.S. Cl. ..... Plt./285

(58) Field of Classification Search ..... Plt./285
See application file for complete search history.

*Primary Examiner* — Susan McCormick Ewoldt
(74) *Attorney, Agent, or Firm* — C. A. Whealy

(57) ABSTRACT

A new and distinct cultivar of *Leucanthemum* plant named 'Engelina', characterized by its compact, upright and mounded plant habit; freely branching habit; strong and upright flowering stems; freely flowering habit; and large double flowers with quilled white-colored ray florets.

2 Drawing Sheets

Botanical designation: *Leucanthemum* hybrid.
Cultivar denomination: 'ENGELINA'.

BACKGROUND OF THE INVENTION

The present invention relates to a new and distinct cultivar of *Leucanthemum* plant, botanically known as *Leucanthemum* and hereinafter referred to by the name 'Engelina'.

The new *Leucanthemum* plant originated from an open-pollination in Thornham Magna, Suffolk, United Kingdom of an unnamed selection of *Leucanthemum* hybrid, not patented, as the female, or seed, parent with an unknown selection of *Leucanthemum* hybrid. The new *Leucanthemum* plant was discovered and selected by the Inventor as a single flowering plant in a controlled outdoor environment in Thornham Magna, Suffolk, United Kingdom in 2000.

Asexual reproduction of the new *Leucanthemum* plant by terminal cuttings in a controlled greenhouse environment in Thornham Magna, Suffolk, Kingdom since 2005 has shown that the unique features of this new *Leucanthemum* plant are stable and reproduced true to type in successive generations.

SUMMARY OF THE INVENTION

Plants of the new *Leucanthemum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Engelina'. These characteristics in combination distinguish 'Engelina' as a new and distinct *Leucanthemum* plant:

1. Compact, upright and mounded plant habit.
2. Freely branching habit.
3. Strong and upright flowering stems.
4. Freely flowering habit.
5. Large double flowers with quilled white-colored ray florets.

Plants of the new *Leucanthemum* differ primarily from plants of the female parent selection in inflorescence form as plants of the female parent selection have single type inflorescences.

Plants of the new *Leucanthemum* can be compared to plants of *Leucanthemum* 'Leumayel', disclosed in U.S. Plant Pat. No. 19,242. In side-by-side comparisons plants of the new *Leucanthemum* differ from plants of 'Leumayel' in the following characteristics:

1. Plants of the new *Leucanthemum* are more compact than plants of 'Leumayel'.
2. Plants of the new *Leucanthemum* and 'Leumayel' differ in inflorescence form as plants of 'Leumayel' have single type inflorescences.
3. Plants of the new *Leucanthemum* and 'Leumayel' differ in ray floret color as plants of 'Leumayel' have light yellow-colored ray florets.

BRIEF DESCRIPTION OF THE PHOTOGRAPHS

The accompanying colored photographs illustrate the overall appearance of the new *Leucanthemum* plant. These photographs show the colors as true as it is reasonably possible to obtain in colored reproductions of this type. Colors in the photographs may differ slightly from the color values cited in the detailed botanical description which accurately describe the colors of the new *Leucanthemum* plant.

The photograph on the first sheet comprises a side perspective view of typical flowering plants of 'Engelina' grown in an outdoor nursery.

The photograph on the second sheet comprises a close-up view of typical inflorescences of 'Engelina'.

DETAILED BOTANICAL DESCRIPTION

The aforementioned photographs and following observations and measurements describe plants grown during the summer in an outdoor nursery in Bressingham, United Kingdom and under commercial practices. During the production of the plants, day temperatures averaged 21° C. and night temperatures averaged 10° C. Plants were three years old when the photographs and the description were taken. In the following description, color references are made to The Royal Horticultural Society Colour Chart, 2007 Edition, except where general terms of ordinary dictionary significance are used.

Botanical classification: *Leucanthemum* hybrid 'Engelina'.

Parentage:

*Female, or seed, parent.*—Unnamed selection of *Leucanthemum* hybrid, not patented.

*Male, or pollen, parent.*—Unknown selection of *Leucanthemum* hybrid, not patented.

Propagation:

*Type.*—Terminal vegetative cuttings.

*Time to initiate roots, summer.*—About 15 days at 21° C. to 25° C.

*Time to initiate roots, winter.*—About one month at 21° C. to 25° C.

*Time to produce a rooted young plant, summer.*—About 20 days at 21° C. to 25° C.

*Time to produce a rooted young plant, winter.*—About three months at 5° C. to 8° C.

*Root description.*—Fine to medium in thickness, fibrous; color, close to 158B.

*Rooting habit.*—Moderate branching, moderately dense.

Plant description:

*Appearance/growth habit.*—Herbaceous perennial; compact, upright and mounded plant habit; moderately vigorous growth habit; freely branching habit with about 70 lateral branches developing per plant.

*Plant height.*—About 55 cm.

*Plant width.*—About 60 cm to 70 cm.

*Lateral branch description.*—Aspect: Mostly upright. Strength: Strong. Length: About 40 cm. Diameter: About 3 mm. Internode length: About 3 cm. Texture: Slightly pubescent; longitudinally ridged. Color: Close to 137A.

*Foliage description.*—Arrangement: Alternate; simple; sessile. Length: About 10 cm to 15 cm. Width: About 3 cm. Shape: Oblanceolate. Apex: Acute. Base: Cuneate. Margin: Serrate. Texture, upper and lower surfaces: Slightly pubescent. Venation pattern: Pinnate. Color: Developing leaves, upper surface: Close to 137B. Developing leaves, lower surface: Close to 137D. Fully developed leaves, upper surface: Close to 137A; venation, close to 137D. Fully developed leaves, lower surface: Close to 137C; venation, close to 137C.

Inflorescence description:

*Appearance.*—Double-type inflorescence form with quilled ray florets and tubular disc florets; inflorescences held upright on strong peduncles; ray and disc florets develop acropetally on a capitulum.

*Fragrance.*—Slightly fragrant, pleasant.

*Flowering response.*—Plants begin flowering about four months after flowering; in the garden, plants flower naturally from July to August in the United Kingdom.

*Postproduction longevity.*—Inflorescences maintain good substance for about 20 to 40 days on the plant and for about one week as a cut flower; inflorescences persistent.

*Quantity of inflorescences.*—Freely flowering habit, about 60 to 80 inflorescences develop per plant.

*Inflorescence size.*—Diameter: About 8 cm. Depth (height): About 3 cm. Disc diameter: About 2.5 cm.

*Inflorescence buds.*—Shape: Flattened spherical. Height: About 4 mm. Diameter: About 1 cm. Color: Close to 137A.

*Ray florets.*—Length: About 3 cm. Width: About 5 mm. Shape: Quilled. Apex: Acute. Base: Fused. Margin: Entire. Texture, upper and lower surfaces: Smooth, glabrous; crinkled. Number per inflorescence: About 270 to 400 arranged in numerous whorls. Aspect: Initially upright to about horizontal with development. Color: When opening, upper surface: Close to 158C. When opening, lower surface: Close to 158D. Fully opened, upper surface: Close to 158B; color becoming closer to 158D with development. Fully opened, lower surface: Close to 158C.

*Disc florets.*—Shape: Fused tubular, erect and elongated. Apex: Acute. Length: About 5 mm. Diameter: About 1 mm. Number per inflorescence: About 150 to 200, massed at the center of the receptacle. Color, when opening: Close to 12A. Color, fully opened: Close to 12B.

*Involucral bracts.*—Length: About 1 cm. Width: About 1 mm. Shape: Lanceolate. Apex: Acute. Base: Cuneate. Margin: Entire. Texture, upper and lower surfaces: Smooth, glabrous. Number per inflorescence: About 55 arranged in several whorls. Color: When opening, upper surface: Close to 147B. When opening, lower surface: Close to 147C. Fully opened, upper surface: Close to 147C. Fully opened, lower surface: Close to 147D.

*Peduncles.*—Length: About 15 cm to 20 cm. Diameter: About 3 mm. Strength: Strong. Angle: Mostly upright. Texture: Slightly pubescent. Color: Close to 137A.

*Reproductive organs.*—Androecium: Quantity per floret: One per disc floret. Anther shape: Oblong. Anther length: About 1 mm. Anther color: Close to 201B. Pollen amount: None observed. Gynoecium: Not observed.

*Seed/fruit.*—Seed and fruit production have not been observed.

Disease/pest resistance: Plants of the new *Leucanthemum* have been observed to be resistant to mildew. Plants of the new *Leucanthemum* have not been observed to be resistant to pests and other pathogens common to *Leucanthemum* plants.

Garden performance: Plants of the new *Leucanthemum* have been observed to have good garden performance and to tolerate wind, rain and temperatures ranging from about −15° C. to about 30° C.

It is claimed:

1. A new and distinct *Leucanthemum* plant named 'Engelina' as illustrated and described.

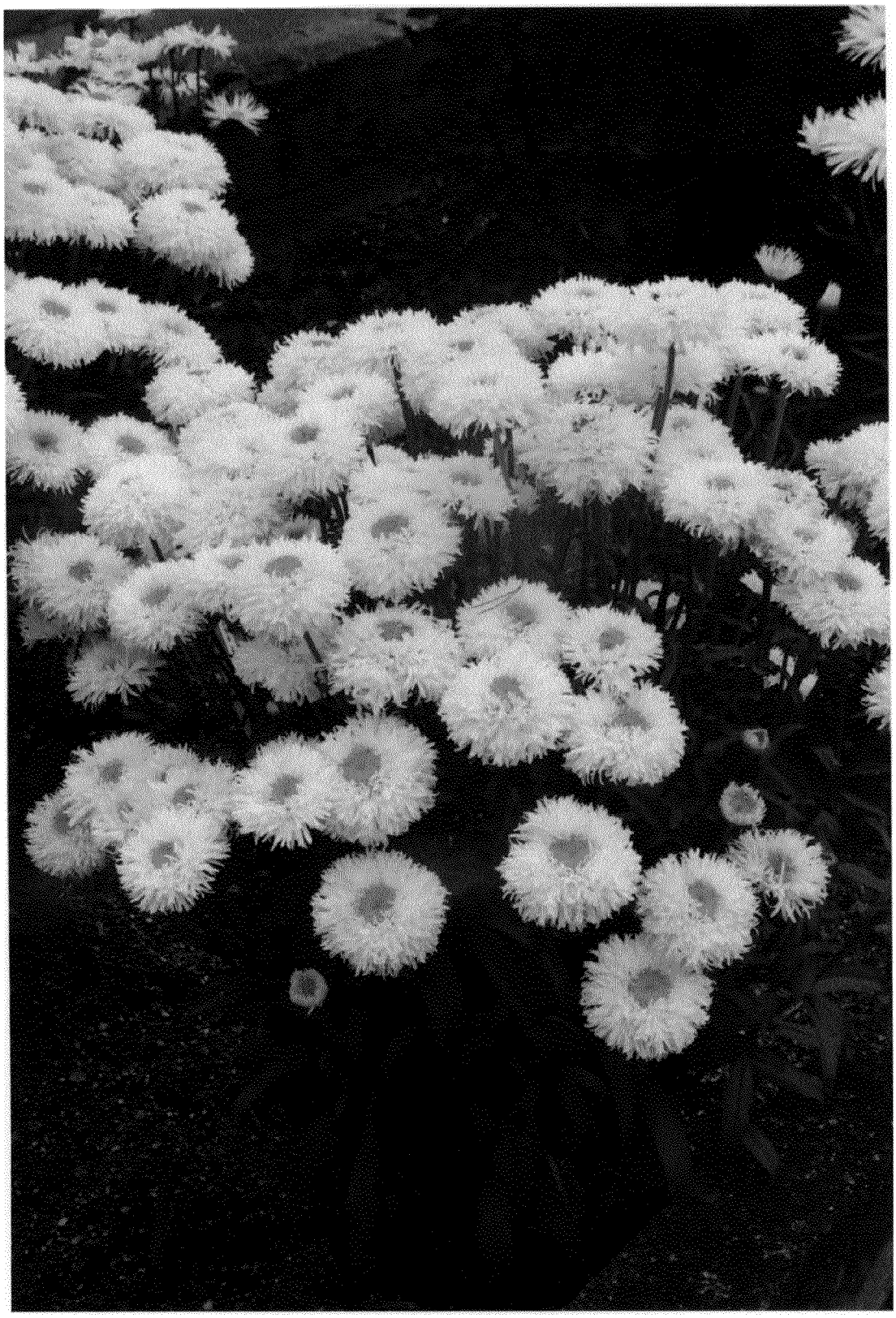

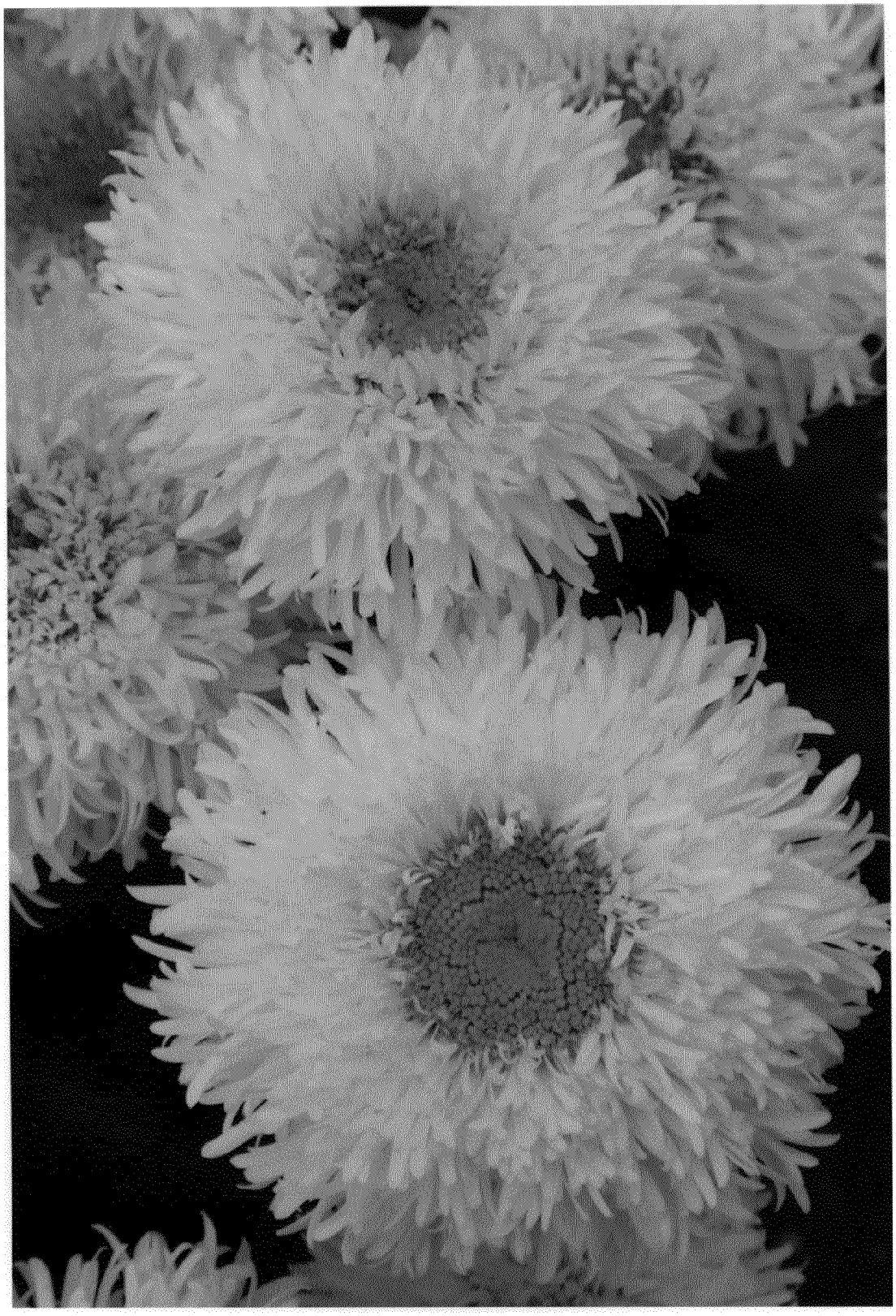

* * * * *